United States Patent [19]
Dunn

[11] Patent Number: 5,387,177
[45] Date of Patent: Feb. 7, 1995

[54] ADJUSTABLE PEDIATRIC INCUBATOR NEST

[75] Inventor: Christopher E. Dunn, Greer, S.C.

[73] Assignee: Span-America Medical Systems, Inc., Greenville, S.C.

[21] Appl. No.: 61,571

[22] Filed: May 13, 1993

[51] Int. Cl.⁶ .......................................... A61G 11/00
[52] U.S. Cl. ............................. 600/22; 128/897; 5/603
[58] Field of Search ............................ 600/21–22; 128/897–898; 5/93.1, 95, 100, 448, 600, 603, 613

[56] References Cited

U.S. PATENT DOCUMENTS

| | | |
|---|---|---|
| D. 214,302 | 6/1969 | Barber . |
| D. 276,938 | 12/1984 | Pedersen . |
| D. 337,217 | 7/1993 | Strickland . |
| 3,729,752 | 5/1973 | Huggins . |
| 3,742,528 | 7/1973 | Munch . |
| 3,854,156 | 12/1974 | Williams . |
| 4,024,861 | 5/1977 | Vincent . |
| 4,583,253 | 4/1986 | Hall . |
| 4,686,725 | 8/1987 | Mitchell . |
| 4,712,258 | 12/1987 | Eves . |
| 4,726,087 | 2/1988 | Schaefer et al. . |
| 4,790,041 | 12/1988 | Shtull . |
| 4,832,007 | 5/1989 | Davis, Jr. et al. . |
| 4,862,538 | 9/1989 | Spann et al. . |
| 4,901,387 | 2/1990 | Luke . |
| 5,025,519 | 6/1991 | Spann et al. . |
| 5,037,375 | 8/1991 | Gatts ....................... 600/21 |

FOREIGN PATENT DOCUMENTS 3502003  7/1986  Germany ................... 600/22

*Primary Examiner*—Angela D. Sykes
*Assistant Examiner*—John P. Lacyk

[57] ABSTRACT

An adjustable pediatric incubator nest includes multiple pieces which may be selectively arranged by a caregiver to protectively partially enclose a pediatric patient on an upper support surface thereof without impeding caregiver access to patient. A resilient base member receives a pair of resilient foam side wall members in a caregiver selected position to cradle a specific patient. Hook and eye complementary type securement features may be used, together with a fabric covering for the resilient base. The top of each side rail includes slits for the placement of smaller diameter patient treatment tubes or lead lines, to facilitate technical support of the patient in an intensive care environment. Segments formed across the top of the side rails between adjacent slits may be selectively cut out for the placement of larger diameter tubes. Different contoured pillows may be provided for selectively supporting specific anatomy, such as the patient's head and neck or the patient's head and torso, for example, to permit the patient to assume a fetal-like position. All nest components may be reconfigured in relation to the base member, for complete adjustability as patient care is periodically reassessed and modified.

41 Claims, 4 Drawing Sheets

ADJUSTABLE PEDIATRIC INCUBATOR NEST

BACKGROUND OF THE INVENTION

The invention concerns pediatric patient care in general and specifically the care of a neonatal intensive care unit patient received in an incubator.

Infants born prematurely or otherwise in ill health frequently require special care (eg., intensive care) in a specialized neonatal nursery. One common form of treatment involves use of an apparatus referred to as an incubator, which is a form of controlled chamber for the care and protection of premature and sick infants. The chamber can be alternatively fully enclosed or partially protected, so as to control the environmental conditions (for example, temperature and sterility) of the infant patient.

An infant being treated in such an incubator may weigh only several pounds (or less), and may be only 18 inches long (or less). At the same time, the delicate infant must often be subjected to a variety of patient treatment devices, such as catheter tubes of various functions, feeding tubes, breathing tubes, and electrode lead lines of various monitoring devices. The tubing and lead lines operatively interconnected with the infant patient must often be taped or similarly secured in place, both as to the infant and in relation to the incubator chamber.

The chamber itself may typically be formed of Plexiglas or other transparent material, and includes relatively deep sides and possibly a closable lid. Within the incubator may be provided a basic mattress or padding, perhaps with a cloth covering or similar. Typically, no special arrangements are provided for support of the delicate infant since the incubator is to a large extent designed to meet the functionality criteria of providing a controlled environment for the patient while accommodating the sometimes considerable technical support for such patient. If a patient needs to be positioned (eg., head raised), a nurse or other caregiver might simply place a rolled or folded towel beneath the padding to raise one end of the infant support.

Heretofore, the number of patient positioning devices concerned with the specific needs of very young pediatric patients have, in general, been relatively limited as compared with the number of specialized patient care products available for other patients. One relatively recent example of a device specifically concerned with pediatric patients is found in an application commonly assigned with the present application, U.S. patent application Ser. No. 07/773,079, filed Oct. 7, 1991, presently allowed, for a design by inventor Mary E. Strickland entitled "Pediatric Body Cradle." In such design, a generally rectangular foam box with fixed sides is provided with one open end to facilitate receipt of a pediatric patient, with foam straps being drawn across the top of the device for protection of the patient.

Other specialized devices for infants or young children, covering from orthodontic cradleboards to baby changing mats and automobile sleepers to various foam mattresses and devices for support of other patients, have been known. The following patents provide examples thereof:

| U.S. Pat. No. | INVENTOR | TITLE |
| --- | --- | --- |
| DES. 214,302 | BARBER | PILLOW |
| DES. 276,938 | PEDERSEN | SURGICAL PILLOW |
| 3,729,752 | HUGGINS | ORTHODONTIC CRADLEBOARD |
| 3,742,528 | MUNCH | MATTRESS FOR INVALIDS |
| 3,854,156 | WILLIAMS | PORTABLE BABY WARMING APPARATUS |
| 4,024,861 | VINCENT | SPINAL SUPPORT |
| 4,583,253 | HALL | BABY SLEEPER FOR AUTOMOBILES |
| 4,686,725 | MITCHELL | MATTRESS CUSHION WITH SECUREMENT FEATURE |
| 4,712,258 | EVES | BABY CHANGING MAT |
| 4,726,087 | SCHAEFER et al. | CONTOURED HEAD AND NECK FOAM PILLOW |
| 4,790,041 | SHTULL | PILLOW FOR RITUAL CIRCUMCISIONS AND METHOD |
| 4,832,007 | DAVIS, JR. et al. | TRACTION PILLOW AND METHOD |
| 4,862,538 | SPANN et al. | MULTI-SECTION MATTRESS OVERLAY FOR SYSTEMATIZED PRESSURE DISPERSION |
| 4,901,387 | LUKE | MATTRESS OVERLAY WITH INDIVIDUAL FOAM SPRINGS |
| 5,025,519 | SPANN et al. | MULTI-SECTION MATTRESS OVERLAY FOR SYSTEMATIZED PRESSURE DISPERSION |

The disclosures of the foregoing patents and the referenced allowed application are fully incorporated herein by reference.

SUMMARY OF THE INVENTION

The present invention recognizes and addresses various of the foregoing problems, and others, concerning the care of pediatric patients. Thus, broadly speaking, a principal object of this invention is improved care of pediatric patients. More particularly, a main concern is improved adjustable pediatric care devices and corresponding improved methods of care using same.

It is another particular object of the present invention to provide an apparatus with adjustable features for the care of a neonatal ICU patient, such as in an incubator.

It is another general object of the present invention to provide improved pediatric patient care which not only provides adjustability for periodically assessing and modifying patient care, but which also facilitates the use and interaction of conventional patient technical support treatment devices such as tubes and lead lines. In such context, it is a more particular present object to provide flexibility and improvement in originally positioning and subsequently repositioning patient care tubes or the like, in relation to an adjustable pediatric incubator nest.

Still a further general object of the subject invention is to provide a multi-adjustable incubator nest which simultaneously protectively partially encloses a pediatric patient without impeding caregiver access to such patient. It is a more particular object to provide such an apparatus which is completely safe for the pediatric patient while also being very simple to use and relatively inexpensive to manufacture. Accordingly, it is a further object of the subject invention to provide considerable improvement in pediatric patient care at a relatively very low marginal cost.

It is yet another particular object of the subject invention to provide the foregoing forms of improved apparatus and corresponding improved methodology of care which accommodates specific needs of an infant patient, for example, such as highly customized support for protection of delicate infant features and for permitting natural resting positions of the newborn such as the fetal position or similar. Therefore, a more particular present object is to accommodate support of a newborn patient with the patient's legs and/or arms partly drawn in towards the torso, and/or to otherwise carefully and protectively support an infant which is both sickly and relatively undeveloped as to skeletal process or muscular strength and control.

Additional objects and advantages of the invention are set forth in, or will be apparent to those of ordinary skill in the art from, the detailed description which follows. Also, it should be further appreciated that modifications and variations to the specifically illustrated and discussed features, materials, and steps hereof may be practiced in various embodiments and uses of this invention without departing from the spirit and scope thereof by virtue of present reference thereto. Such variations may include, but are not limited to, substitution of equivalent means and features, materials, or steps for those shown or discussed, and the functional or positional reversal of various parts, features, steps, or the like.

Still further, it is to be understood that different embodiments, as well as different presently preferred embodiments, of this invention may include various combinations or configurations of presently disclosed features, elements, or steps, or their equivalents, including combinations of features or steps or configurations thereof not expressly shown in the figures or stated in the detailed description herewith. One exemplary such embodiment of the present invention relates to an adjustable pediatric incubator nest, comprising a resilient base member and a pair of adjustable side wall members. Preferably, such base member has an upper support surface for receiving a pediatric patient thereon, and first securement means provided on such upper support surface for removably securing further nest members thereto at selected positions thereon. The pair of adjustable side wall members are preferably formed of resilient foam, and have respective lower support surfaces with respective second securement means thereon for selectively cooperating with the first securement means for removably securing such side wall members to the base member upper support surface, with the side wall members adjustably positioned in substantially opposing relationship to one another at a selected interval. With such an arrangement, the side wall members protectively partially enclose a pediatric patient on the upper support surface without impeding caregiver access to such patient.

Another present exemplary embodiment concerns a multi-piece infant foam cradle, comprising in combination a main support base, a first layer of material, at least one adjustable side rail means, and pillow means.

In the foregoing foam cradle embodiment, preferably the main support base is comprised of resilient foam and has an infant support surface formed on an upper side thereof. The first layer of material is received on the support base upper side and provides a surface texture for selective securement of further cradle components thereto.

The adjustable side rail means comprises a generally elongated resilient foam member with securement means thereon for selectively positioned removable securement of such side rail means to the first layer of material. In such manner, the side rail means adjustably protects an infant received on the infant support surface. A second similar side rail means could be used to protect an opposite lateral side of the infant. The pillow means preferably comprises a resilient foam member with securement means thereon for selectively positioned removable securement of such pillow means to the first layer of material. With such features, the pillow means adjustably supports a selected body region of an infant received on the infant support surface.

Yet another construction comprising a present exemplary embodiment includes a multi-piece multi-adjustable incubator nest for a neonatal ICU patient, such incubator comprising in combination a generally rectangular base mattress, a fabric layer, a pair of adjustable side rails, and at least one patient pillow.

In such incubator nest exemplary embodiment, preferably the mattress comprises resilient foam of predetermined support characteristics and has an upper side patient support surface, such patient support surface having a predetermined arrangement of support elements formed therein and providing generally planar patient support. The fabric layer is preferably received on such patient support surface and comprises fabric for one of hook and eye complementary type securement elements substantially covering the patient support surface.

Still further, the pair of adjustable side rails may be generally elongated and comprise resilient foam having respective curved side surfaces for positioning on opposite sides of a patient received on the patient support surface for protectively partially enclosing such patient. The side rails also have respective generally flat bottom support surfaces with one of hook and eye complementary type securement elements thereon so that such side rails may each be selectively removably secured to the fabric layer positioned at desired respective locations on the patient support surface. They also have respective top surfaces a predetermined distance above their bottom support surfaces. Such top surfaces include openings therein for the passage and securement of treatment tubes and apparatus for an ICU patient supported in the incubator nest.

The foregoing at least one patient pillow comprises resilient foam and preferably has a predetermined contoured shape for supporting a preselected corresponding body portion of a patient received on the patient support surface. It also has a generally flat bottom support surface with one of hook and eye complementary type securement elements thereon so that such pillow may be selectively removably secured to the fabric layer positioned at a desired location on the patient support surface.

It is to be understood that this present invention likewise concerns corresponding methodology for use of improved apparatus in accordance with the subject invention, resulting in improved methods of care. One exemplary embodiment of such concerns a method of care for a neonatal ICU patient through use of a multi-piece multi-adjustable incubator nest, which includes a generally rectangular base mattress of resilient foam and having an upper side patient support surface; a fabric layer received on the patient support surface and comprising fabric for one of hook and eye complementary type securement elements substantially covering the patient support surface; a pair of generally elongated adjustable side rails comprising resilient foam and having respective generally flat bottom support surfaces with one of hook and eye complementary type securement elements thereon; and at least one patient pillow comprising resilient foam and having a generally flat bottom support surface with one of hook and eye complementary type securement elements thereon.

The above-referenced exemplary method further involves selectively positioning the described side rails on opposite sides of a patient received on the patient support surface with the side rails spaced from one another a selected distance so as to protectively partially enclose the patient without impeding caregiver access thereto. Thereafter, the side rails are removably secured in their selected positions by pressing the respective side rail bottom support surfaces onto the fabric layer. Such action engages their respective complementary type 0 securement elements.

The exemplary method still further involves selectively positioning the described pillow so as to support a portion of the body of a patient received on the patient support surface. Next, such pillow is removably secured in its selected position by pressing the pillow bottom support surface onto the fabric layer for engagement of their respective complementary type securement elements.

It is to be understood that such exemplary method, and others, of the subject invention greatly facilitates and improves the ability of a caregiver to periodically subsequently assess and adjust the selected positions of the side rails and the pillow so as to optimize patient care in an ICU incubator in which the patient is received. Other present features, as discussed hereinafter, provide other advantages and improvements in care methodology, such as in the area of accommodating technical support needs of an incubator patient.

Those of ordinary skill in the art will better appreciate the features and aspects of such embodiments, methodologies, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures, in which:

FIG. 1 is a perspective view of a first exemplary embodiment of the present invention illustrating use thereof with conventional patient treatment tubing or the like;

Figure 1:
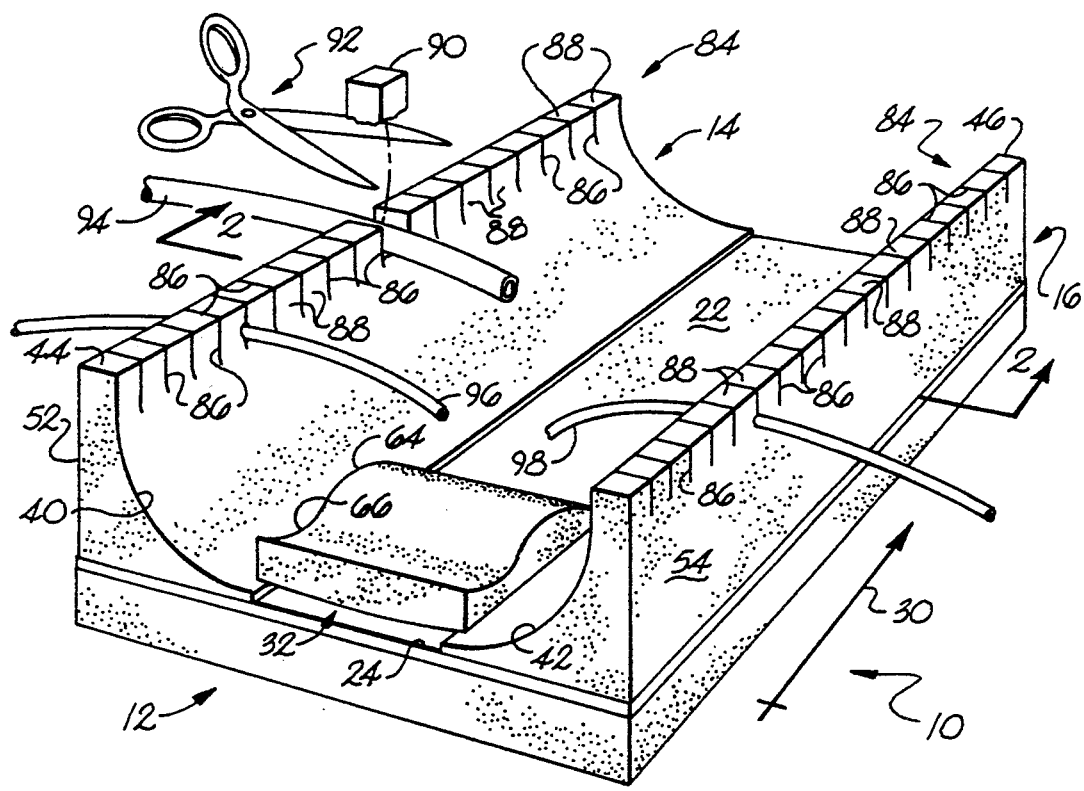

Repeat use of reference characters throughout the present specification and appended drawings is intended to represent same or analogous features, elements, or steps of the invention.

DETAILED DESCRIPTION OF THE PREFERRED EMBODIMENTS

It is to be understood that the following discussion relates to detailed descriptions of presently preferred exemplary embodiments only, and is not intended as limiting the broader aspects of the subject invention as disclosed herewith, or as represented by these embodiments. Therefore, specific embodiments covered by the subject invention may have different appearances, dimensions, etc. from those shown and discussed hereinafter. As a first example of the subject invention, one presently preferred adjustable pediatric incubator nest 10 is shown in perspective view, from a generally top and side perspective, in present FIG. 1. FIG. 2 illustrates a cross sectional view of the exemplary embodiment 10 of present FIG. 1, taken along the sectional line 2—2 as indicated therein.

More specifically, such adjustable pediatric incubator nest or multi-piece infant foam cradle 10, is multiply adjustable for use such as with a neonatal ICU patient, and in accordance with a method of care using nest or cradle 10 per this invention.

Nest or cradle 10 may variously include combinations of different components in accordance with this invention. For example, a resilient base member generally 12 may be provided in combination with one or more of resilient foam adjustable side wall members or side rail means generally 14 and 16. As shown by respective exemplary double-headed arrows 18 and 20, the positions of adjustable side wall members 14 and 16 may be freely and continuously adjusted in relation to an upper support surface 22 of resilient base member 12. Surface 22 is also adapted for receiving a pediatric patient thereon. With such an arrangement, one of the important objects of the subject invention is achieved, through the present methodology of appropriately positioning one or more side wall members such as 14 and 16 in relation to the patient support surface 22 (through the use of securement means, such as discussed below).

Generally speaking, resilient base member 12 serves as a platform on which other components of a multi-piece cradle or incubator nest in accordance with the invention may be placed and secured. Various securement means may be practiced for removably holding such components in caregiver selected arrangements.

For example, strippable adhesives, double-sided tape, snaps, or other arrangements may be practiced. However, it is generally preferred to make use of respective hook and eye complementary type securement elements, such as available under the trademark "Velcro." In any instance, securement features of one component in accordance with the present invention may be provided with either the hook or eye complementary securement elements or features, for operative interconnection and cooperation with the complementary one of the hook and eye elements on an opposing component to which the first component is to be applied. For example, base member 12 may be provided with either hook or eye elements, with the other components to be secured thereto provided with the opposite type of securement element.

However, in the presently preferred exemplary embodiment, a first layer of material, generally 24, is received on the support base 12 upper side 22, so as to provide a fabric with a suitable surface texture for selective securement of further cradle components thereto. One example of an appropriate fabric could be a brushed knitted fabric, to which the hook securement features of a hook and eye arrangement readily but removably adhere. If such a fabric 24 is provided over the entire surface of top side 22, all components will have essentially continuously variable positions for periodic reassessment and adjustment of pediatric patient care conditions. In some embodiments, it may not be necessary for fabric 24 to cover the entire surface area of patient support surface 22 in order to provide an adequate or desired level of adjustability in given circumstances.

while various embodiments may be practiced, resilient base member 12 preferably comprises a generally rectangular base mattress or main support base comprised of resilient foam. Such foam may have the same or different characteristics as the other foam components of the incubator nest 10. For ease of manufacture, fabric 24 may be initially secured to a first layer of foam 26, which is then laminated to a second, generally thicker, layer of foam 28 so as to collectively comprise resilient base member 12. Foam layer lamination technology is generally well known to those of ordinary skill in the art without further discussion, the details of which technology form no particular aspect of the subject invention.

Preferably, support base 12 is provided in a generally rectangular form so as to match closely with an incubator chamber in which it is intended to be inserted. Therefore, the length and width of base member 12 preferably is made to match a specific incubator nest in which it is to be used. However, it will be readily apparent to those of ordinary skill in the art, from the complete description and disclosure herewith, that an incubator nest such as exemplary cradle 10 in accordance with this invention can likewise provide useful and effective service in circumstances outside those of an incubator chamber. Therefore, the broader aspects of the subject invention are not expressly limited to use within an incubator nest, nor dimensional sizes restricted to those as would be accommodated within an incubator chamber.

Figure 2:
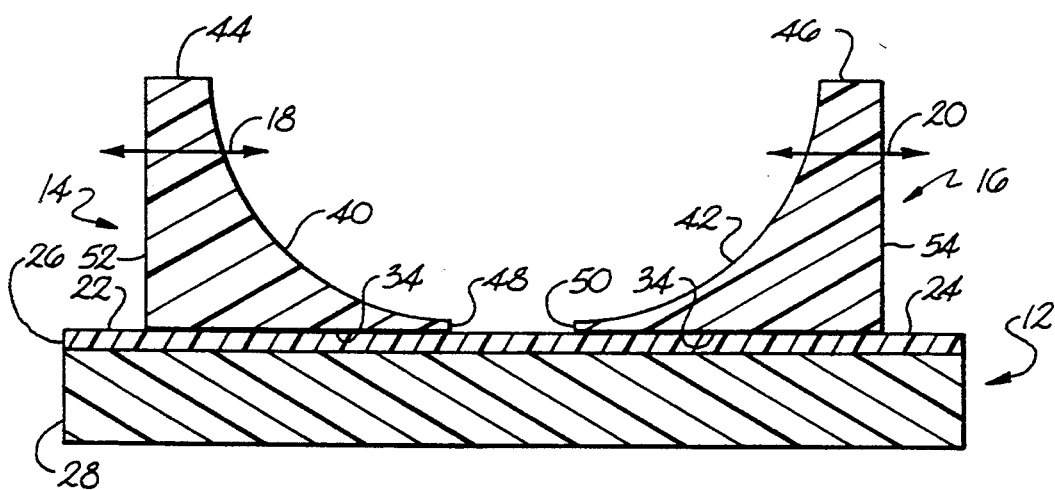
FIG. 2 is a cross-sectional view of the exemplary embodiment of present FIG. 1, taken along the sectional line 2—2 therein.

At the same time, the exemplary embodiment 10 of present FIGS. 1 and 2 is preferably sized for insertion into an incubator chamber, and has a length (along the direction of the longitudinal axis 30) of about 19 inches and a width perpendicular thereto of about 11 inches. The full base member 12 has a thickness of about 1.5 inches, with foam layer 26 comprising about 0.25 inches of such total. In accordance with the broader aspects of the subject invention, the length of base member 12 may more broadly fall in a range generally from about 15 inches to about 30 inches, or even other dimensions, while the width more broadly may fall in a range generally from about 10 inches to 15 inches, and the predetermined thickness may include a variety of thicknesses, preferably of at least generally about 1 inch total.

Some embodiments of the subject invention may also include as a component thereof pillow means generally 32, comprising at least one patient pillow formed from a resilient foam member, and having some form of securement means (for example, as discussed above) carried thereon for selective positioning thereof removably secured to the first layer of material generally 24 on base member 12. With such an arrangement, the pillow means generally 32 adjustably supports a selected body region of an infant received on the infant support surface 22. As discussed in greater detail below, various arrangements of pillow means may be provided, and may be likewise variously contoured for supporting different preselected portions of a pediatric patient's body.

Figure 3:
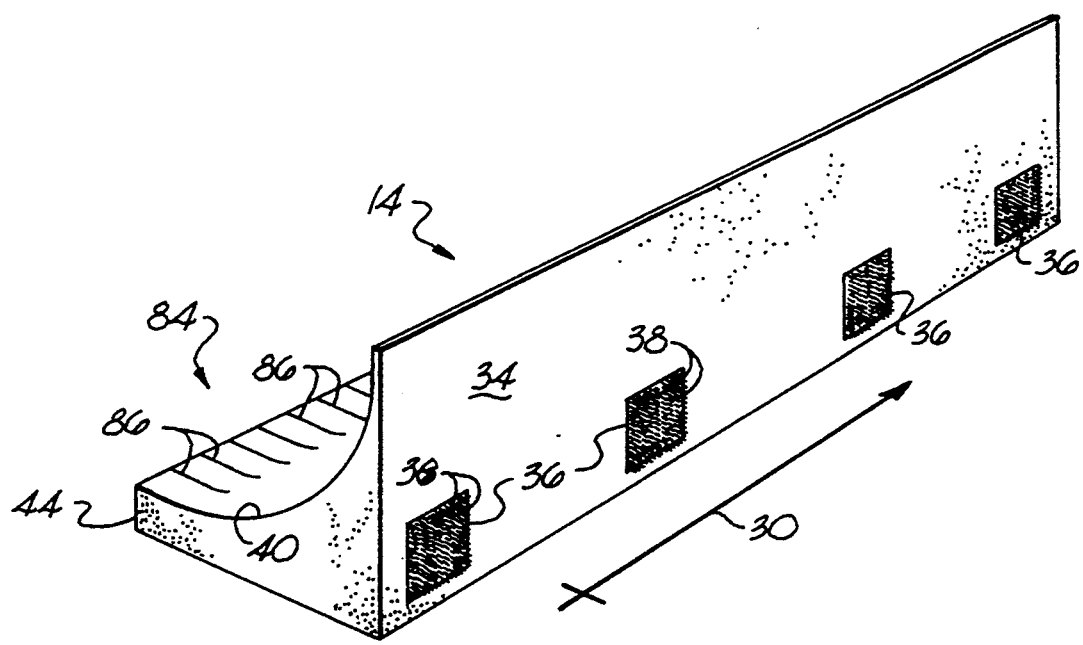
FIG. 3 is an isolated perspective view of an exemplary adjustable side rail means in accordance with the subject invention, shown primarily from the perspective of a bottom support surface thereof.

FIG. 3 illustrates an isolated perspective view of an exemplary side rail means, generally 14, in accordance with the subject invention. In such view, side wall member 14 has been rotated counterclockwise 90 degrees along its lengthwise axis 30, in relation to the illustration thereof shown in present FIG. 1. Otherwise, the position thereof is generally the same. For purposes of present disclosure, the other adjustable side wall member 16 may be regarded as a mirror image (structurally) of adjustable side wall member 14. However, in some embodiments of the subject invention, only one adjustable side wall member might be used, with no other side wall member utilized, or with a fixed side wall member otherwise used, or with a different embodiment of an adjustable side wall member utilized.

As illustrated in FIG. 3, exemplary adjustable side wall member 14 is provided with a respective lower support surface 34, which is generally flat so as to be received on the generally planar patient support surface 22 of base member 12. In the nest embodiment 10 of present FIGS. 1 and 2, such surface 22 is also relatively flat, though other surface arrangements may be provided resulting in a generally planar patient support surface 22 in accordance with this invention, such as discussed below with reference to present FIG. 7.

The first layer of material 24, or other means, may be regarded as a first securement means in accordance with the subject invention, with second securement means in accordance with this invention being supported on the lower support surface 34 of an adjustable side wall member such as 14. For example, a plurality of patches or the like 36 may be provided for supporting one of hook and eye complementary type securement elements. Preferably hook elements such as 38 would be used whenever first layer of material 24 is provided as a brushed knitted fabric or the like. With such an arrangement, the position of adjustable side wall member 14 is essentially continuously variable (i.e., adjustable) in relation to patient support surface 22 of base member 12. Other placements and arrangements of second securement means or the like may be practiced, as referenced above.

Though not illustrated in present FIGS. 1 and 2, the securement means illustrated in present FIG. 3 may be utilized by a caregiver (such as a nurse or other healthcare professional) so as to secure the caregiver selected positions of adjustable side wall members 14 and 16 relative to base member 12. As represented therein, preferably such adjustable side wall members are adjustably positioned in substantially opposing relationship to one another and at a selected interval (i.e. separation distance therebetween), such that the side wall members protectively partially enclose a pediatric patient on upper support surface 22 without impeding caregiver access to such patient.

As further shown in present FIGS. 1 through 3, each adjustable side wall number 14 or 16 preferably has at least one respective lateral side wall, such as 40 and 42, respectively, which has a predetermined slope thereto, interconnecting between bottom support surfaces 34 thereof and a top surface or wall thereof, generally 44 and 46, respectively. As shown, members 14 and 16 may be turned so that such sloped lateral side walls 40 and 42 are situated relatively opposite to one another with a patient received therebetween on the base member upper support surface 22.

Though different embodiments may be practiced, such sloped lateral side walls 40 and 42 also preferably have a radius of curvature associated therewith, which diminishes the thickness of members 14 and 16 to generally less than about 0.25 inches at edges 48 and 50 thereof adjacent to the intersection of the lower support surfaces 34 and the patient support surface 22. Such a dimension is adequate to permit a smooth flow as to any patient contact along such edges 48 and 50, while at the same time being thick enough to avoid manufacturing problems. Resilient foam is known to have an adverse so-called "feathering" effect if it is cut dimensionally so as to be very thin.

As further shown in the Figures, each lateral side wall 40 and 42 has a generally opposing lateral side wall 52 and 54, respectively. While different shapes may be practiced, such side walls preferably rise generally vertically from lower support surfaces 34 to top surfaces or walls 44 and 46. As shown, the opposing pairs of first and second lateral side walls (40/52 and 42/54) both rise from their lower support surfaces 34 and terminate in their respective top walls or surfaces 44 and 46. Such arrangement results in the overall configuration of the adjustable side rail means or side wall members 14 and 16.

As shown best in FIGS. 1 and 2, the upper side wall surfaces 44 and 46 of side wall members 14 and 16, respectively, are at a predetermined height above the base member upper support surface 22, which height preferably falls in a range generally such as from about 2 inches to about 5 inches. In the specific embodiment shown, a height of about 3 inches (i.e., the represented height of lateral side walls 52 and 54) is preferred.

Still further, the base member 12 and side wall members 14 and 16 may comprise resilient foam members having various characteristics. For example, the density of the foam for base member 12 may be about 1.1 to 1.2 pounds per cubic feet, with essentially the same density foam used for elongated foam members 14 and 16. Such foam components may be provided with a 25% ILD (indentation load deflection) characteristic in a range of from about 15 pounds to about 24 pounds. The terminology 25% ILD characteristic is standard industry terminology meaning the number of pounds of pressure required as an indenting load on a 50 square inch circular plate to deflect a foam member under such plate 25% of the unloaded predetermined thickness of such foam member.

While the foregoing characteristics are provided in conjunction with the specific example illustrated, it is to be understood that other embodiments of the subject invention may more broadly encompass a range of such characteristics. For example, a density may be predetermined so as to fall in a range generally from about 1 to about 1.6 pounds per cubic foot, while the 25% ILD characteristic may more broadly fall in a range generally from about 10 pounds to about 30 pounds. Also, other embodiments may even have other characteristics, and still further embodiments may have different foam characteristics for different foam components collectively comprising an adjustable nest or cradle in accordance with a single embodiment of the subject invention.

Figure 4:
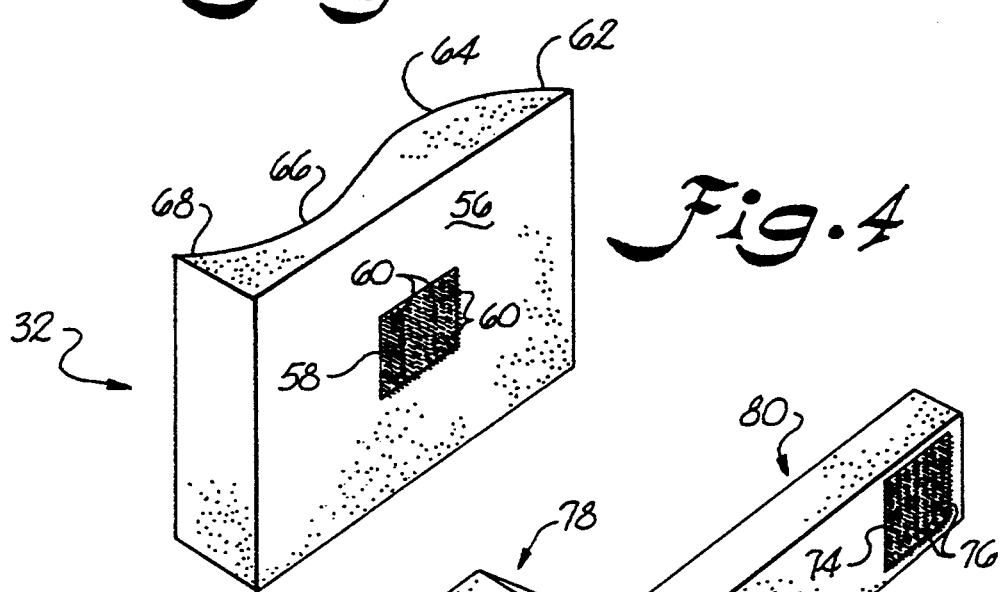
FIG. 4 is an isolated perspective view of one exemplary pillow means in accordance with the subject invention, such as for supporting the head and neck of a pediatric patient, shown primarily from the perspective of a bottom support surface thereof.

FIG. 4 illustrates an isolated perspective view of exemplary pillow means generally 32 in accordance with the first embodiment thereof per the subject invention. Similar to the form of illustration of present FIG. 3, the FIG. 4 illustration (in relation to the illustration of pillow means generally 32 in FIG. 1) has been rotated counterclockwise 90 degrees along the lengthwise axis 30.

As shown in present FIG. 4, the patient pillow generally 32 preferably comprises a resilient foam member 62 having a generally flat lower support surface 56 which supports thereon a third securement means, such as exemplary patch 58 of hook securement features 60. As before, other securement means may be practiced, or an equivalent of member 58 may be otherwise provided on the bottom surface 56 of pillow means 32. However, the arrangement of present FIG. 4, as represented by FIG. 1 during use thereof, permits generally continuously variable adjustability of the relative position of pillow means 32 with reference to patient support surface 22. Of course, some overlap of pillow 32 over edges 48 and 50 of the side wall members may occur (as shown), but third securement means 58 must at all times have access to the remaining open area of patient support surface 22 so as to engage same (unless other arrangements are provided).

As further shown in the exemplary embodiment of present FIG. 4, the patient pillow generally 32 comprising a foam member 62 has a predetermined shape, which may be removably secured to upper support surface 22 with the securement features 58. With such an arrangement, the pillow may adjustably support a selected body region of a patient which corresponds with the predetermined shape thereof.

In the specific embodiment of exemplary pillow 62 of present FIG. 4, at least one relative lobe 64 and one relative trough 66 are provided generally for supporting the neck and head, respectively, of a pediatric patient received thereon. A further relative lobe 68 may be at least partially provided, as illustrated. Other alternative features may be practiced for the subject pillow 62, or other pillow means in accordance with the subject invention. See, for example, the head and neck support surface arrangements as disclosed in commonly assigned U.S. Pat. No. 4,726,087, entitled "Contoured Head and Neck Foam Pillow," the complete disclosure of which is fully incorporated herein by reference, and which features may be adapted for use herewith.

Figure 5:
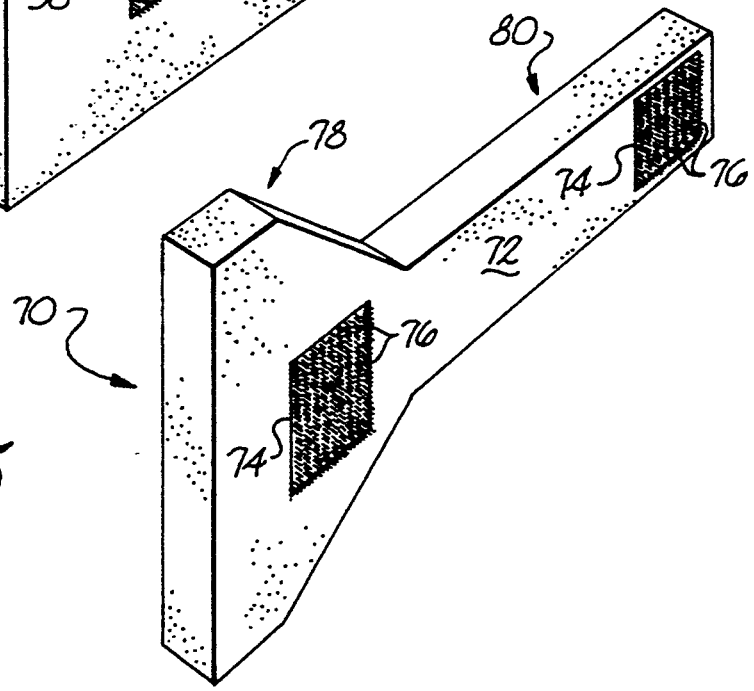
FIG. 5 is an isolated perspective view of exemplary pillow means per an alternate embodiment thereof in accordance with the subject invention, such as for supporting the head and torso of a pediatric patient, shown primarily from the perspective of a bottom support surface thereof.
Figure 6:
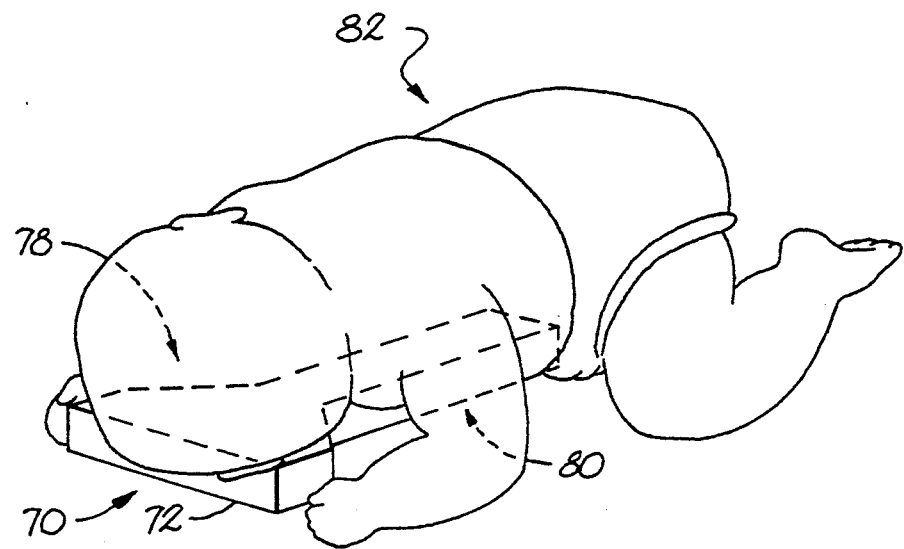
FIG. 6 is an isolated view, from a generally top and side perspective, of the exemplary pillow means embodiment of present FIG. 5, shown in exemplary use thereof for supporting the head and torso of a representative typical pediatric patient in a partially fetal position (i.e., legs partially drawn inward)

FIGS. 5 and 6 illustrate further exemplary pillow means generally 70 which may be practiced in accordance with the subject invention as follows. Such pillow means 70 may be provided as an alternative to pillow means 32, or in addition thereto for selected substitute use by a caregiver, with a specific patient.

FIG. 5 illustrates a generally isolated perspective view of pillow means 70, shown primarily from the perspective of a bottom support surface 72 thereof. Again, patches 74 of hooks securement features 76 form one preferred example of securement means in accordance with the subject invention, though variations and substitutions as discussed above may be practiced.

The illustrated exemplary pillow 72 includes a generally T-shaped cross-section, with a relatively broadened first section 78 thereof generally for supporting a patient's head and with a relatively elongated second section 80 thereof generally for supporting a patient's torso, all as represented in present FIG. 6. For clarity, features in accordance with the subject invention other than pillow 70 are not shown with the use of a representative pediatric patient 82. Such patient 82 is generally in a fetal-like position, with the legs, and to an extent the arms, drawn inwardly towards the body. Whenever patient 82 is also in a prone position (i.e., generally face or torso down), pillow means 70 helps evenly support and comfort pediatric patient 82, as shown. With such an arrangement, a single pillow is provided with a predetermined shape for supporting both the head and torso body regions of the pediatric patient. Other pillow arrangements may be practiced, as discussed below.

As to dimensional aspects of the pillow embodiments of present FIGS. 4 through 6, it should be apparent that dimensions of specific embodiments may vary depending both on the predetermined body portion intended to be supported by a given pillow embodiment, and by the relative size of a given patient. Typical pediatric patients with which the invention might be used may vary considerably in size, weighing anywhere from several pounds (or less) and having a length of 18 inches (or less). Of course, greater or lesser weights, lengths, etc. will also be experienced with specific patients.

In the exemplary pillow embodiment 32 of FIG. 4, the predetermined contoured surface results in the patient pillow having a predetermined varying thickness falling in a range generally from about 0.5 inches to about 2 inches. The thickness means the distance between the bottom support surface 56 and the contoured patient receiving surface opposite thereto. A predetermined width is provided in a range generally from about 3 inches to about 8 inches, and a predetermined length in a range generally from about 4 inches to about 10 inches. In the embodiment illustrated, lobes 64 and 68 have a thickness of about 1 inch, with a thickness of about ⅜ of an inch for relative trough 66, while pillow width is about 4 inches and length is about 5.25 inches. In another exemplary preferred embodiment, the length may be stretched out to about 7.33 inches, and the width to about 6 inches, which pillow would preferably be used with generally larger embodiments of incubator nest 10. The relative positions of the lobes and trough and the curvature of the contoured upper surface would change accordingly.

A presently preferred exemplary pillow such as 70 in present FIGS. 5 and 6 may more broadly have a predetermined thickness in a range generally from about 0.5 inches to about 3 inches, a predetermined length in a range of generally from about 6 inches to about 20 inches, a predetermined width in the relatively broadened first section 78 thereof in a range generally from about 3 inches to about 8 inches, and a predetermined width in the relatively elongated second section 80 thereof in a range generally from about 1 inch to about 5 inches. In one specific exemplary embodiment, the overall length is about 8.5 inches, the width in relatively broadened first section 78 is about 4.75 inches, and the width in relatively elongated second section 80 is about 1 and ⅜ inches. The thickness is about 1.25 inches in such exemplary embodiment.

The foam utilized in exemplary pillows 62 and 70 may have the characteristics in the ranges discussed above, or other characteristics in some embodiments.

Returning attention to present FIGS. 1 and 3, further features of some present exemplary embodiments are shown. Such features, which may be optional to some embodiments, relate for example to patient treatment tube securement means generally 84. Such means 84 are preferably generally integrally formed with the adjustable side wall members, such as elongated foam members 14 and 16. As shown primarily in present FIG. 1, such patient treatment tube securement means generally 84 provide for removable and adjustable securement of at least one patient treatment tube passed therethrough.

More specifically, each of the respective upper side wall surfaces 44 and 46 of the respective exemplary adjustable side wall members 14 and 16 may have a plurality of slits 86 integrally formed therein. Such slits 86 also preferably extend a predetermined depth downwardly from the respective upper side wall surfaces, i.e., towards the bottom support surfaces 34.

As further evidenced by present FIGS. 1 and 3, such exemplary plurality of slits 86 also integrally form a corresponding plurality of selectively removable side wall member segments 88, between adjacent pairs of such slits 86. FIG. 1 illustrates removal of one such side wall member segment 90. Since the entire patient treatment tube securement means generally 84 is comprised preferably of resilient foam material, conventional scissors 92 or other cutting devices, such as a knife or the like, may be used to simply cut away a selected segment 88 in the instance of care for a particular patient with multi-piece infant foam cradle 10.

Through the selective removal of one or more of such segments 88 (such as exemplary segment 90 of present FIG. 1), relatively larger diameter patient treatment tubes (such as tube 94 of present FIG. 1) may be passed through the side wall member 14 so as to operatively interconnect between a patient received on patient support surface 22 and some machine, device, or other form of gas of fluid source or machinery otherwise associated with tube 94. At the same time, relatively smaller diameter patient treatment tubes, such as representative tubes 96 and 98, may be removably and adjustably received in a relative interference fit in respected ones of the slits 86.

It will be readily apparent to one of ordinary skill in the art that the foregoing arrangement works equally well with electronic lead lines or the like, such as may be associated with monitoring equipment to which a pediatric patient is subjected.

It should likewise be readily apparent from the foregoing disclosure and the accompanying drawings herewith that, through the provision of a plurality of such slits, relatively smaller diameter patient treatment tubes or lead lines may be secured in the above-described fashion in virtually any location along adjustable side rails 14 and 16. The flexibility in such variations depends on the number and placement of the subject slits, which may be varied in different embodiments in accordance with this invention, or in a given embodiment thereof.

In the exemplary embodiment of present FIGS. 1 and 3, the exemplary slits are on a predetermined spacing of about 1 inch, and are provided with a depth of about 1.5 inches. In some embodiments of the subject invention, the spacing between adjacent slits may fall in a range generally from about 0.5 inches to about 2 inches, including variations in spacing within a given embodiment. The depth may likewise vary from approximately 0.5 inches to about 2 inches. Other numerical values may be practiced in some embodiments.

It should be apparent that the size of segments 88 primarily is determined by the placement of adjacent slit pairs. In most embodiments, the creation of such slits through direct cutting steps will not result in a significant gap between adjacent segments. Such an arrangement helps promote a relative interference fit upon insertion of tubes such as 96 and 98. In other embodiments, some degree of separation between adjacent segments may preferably be provided, by expanding the width of the respective slits, or by otherwise removing portions of foam material between adjacent areas to be defined as removable side wall member segments. The details of foam cutting technology are generally well known to those of ordinary skill in the art without further discussion, and such details form no particular aspect of the subject invention.

It should be further apparent from the foregoing disclosure that advantageous methods of use in accordance with the subject invention may include steps relating to such patient tube securement means, so as to achieve certain present objects in conjunction with facilitating the integration of technical support for a pediatric patient with protective care and physiological support of the patient's body. The arrangement as illustrated provides a caregiver considerable flexibility for adaptation to different circumstances, while minimizing the need for tape or similar artificial restraints to be applied directly to the patient's body or to an incubator with which the subject invention may be used (or in a hospital bed or other similar arrangement). Of course, practice of this invention does not preclude the use of tape or the like to further secure tubing to an incubator or bed to prevent such from being accidentally pulled out of place, even if tape is not required in order to secure the tubing or leads to a patient's body.

Figure 7:
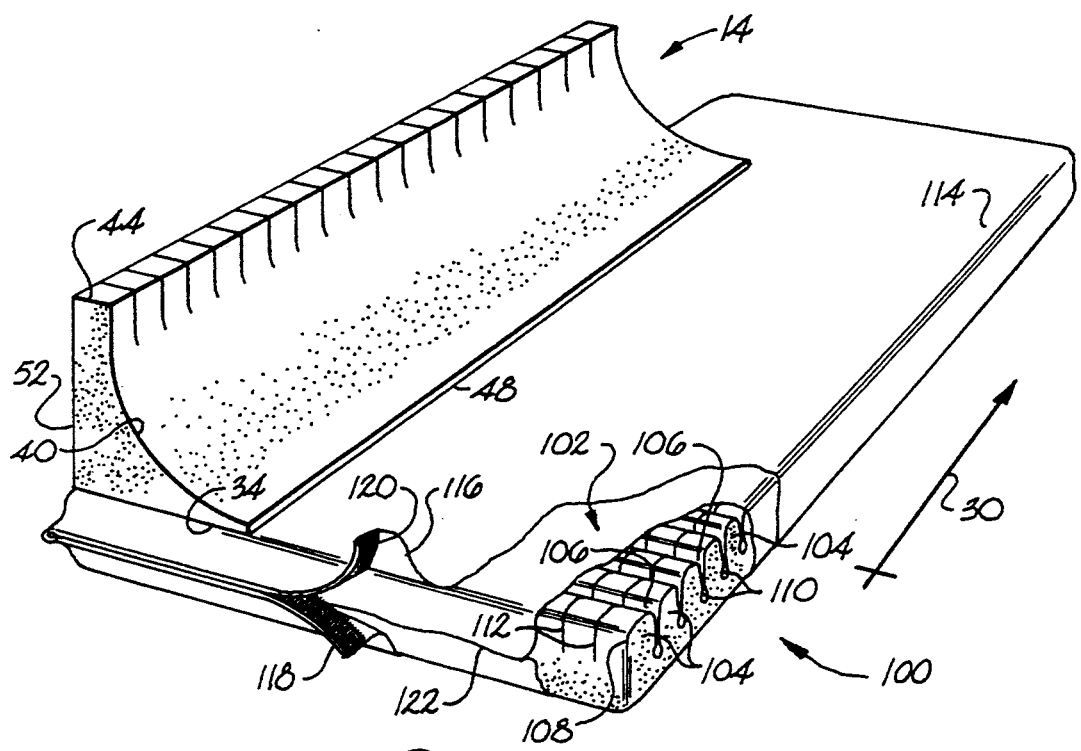
FIG. 7 is a perspective view of a further exemplary embodiment in accordance with the subject invention, having an alternative main support base embodiment, shown with partial cut away of an exemplary securement means layer in accordance with this invention, and used with a single adjustable side rail means in accordance herewith.

FIG. 7 illustrates a generally top and side perspective view of a second exemplary embodiment generally 100 of a resilient base member in accordance with the subject invention. Such second embodiment of a resilient base member 100 also has a generally planar patient support surface 102, but such is not necessarily a generally flat surface as in the case of the first embodiment of base member 12. Instead, the upper support surface of base member 100 comprises a contour cut patient support surface generally 102. Such surface may have a plurality of individual patient support cells 104 integrally formed therein. Such cells may be formed in regular patterns, such as aligned rows, both longitudinally and laterally. Also, air channels generally 106 may be integrally formed between adjacent of such aligned rows of cells 104. Such contour cuts may include rounded edges generally 108 adjacent to the upper surface 102. In addition, generally circular air channels 110 may be provided integrally formed by adjacent bases of individual patient support cells 104.

Longitudinal slits 112, (i.e., cuts in the direction of longitudinal axis 30) may be optionally provided so as to form the longitudinal rows of individual cells. Generally speaking, a number of variations may be practiced in accordance with the subject invention, and the complete disclosures of commonly assigned U.S. Pat. Nos. 4,862,538; 4,901,387; and 5,025,519 are fully incorporated herein by reference, as to further illustration of examples of various alternative configurations which may be practiced. As shown therein, different parts of a patient's body (i.e., different parts of base mattress 100) may be provided with different support characteristics in different embodiments included in broader aspects of the subject invention. It is expected, without further discussion, that practitioners of the subject invention may select specific embodiments thereof to suit anticipated patient needs, without departing from the spirit and scope of this invention.

The overall dimensions of base member 100 may fall within the more broadly described ranges stated above. However, one exemplary length thereof (i.e., the distance along the lengthwise axis in the direction of axis 30) may be about 26 inches, while one exemplary width perpendicular thereto may be about 13 inches. Along such longitudinal axis 30, contour cuts may be made such that the resulting distance between adjacent centers of circular air channels 110 may be about 1 inch. Where, for example, such distance is seven-eighths of an inch, with a 0.25 inch diameter circular air channels, the radius of curvature illustrated along edges 108 results in an individual cell approximately 0.75 inches long (in the direction of axis 30) adjacent the top thereof near edges 108, with a 0.25 inch gap between adjacent cells. At its narrowmost part of separation, i.e., just above circular air channels 110, the separation gap is approximately one-eighth of an inch in such an embodiment. Where practiced, longitudinal slits 112 may be set approximately two inches apart (or less), so that the cells have a corresponding width of about 2 inches (or less) in the lateral or width dimension of pad 100.

For purposes of present discussion and disclosure, a single adjustable side wall member 14 is represented in present FIG. 7, as may be practiced with the subject invention. As is noted above, alternative forms of such side rail may be practiced instead, or such a single side rail 14 may be practiced by itself, or with another such adjustable side rail, or in combination with a fixed position side rail, or in combination with another adjustable side rail of a different configuration. It should also be readily apparent from present FIG. 7 that repositioning of member 14 to the opposite lateral edge 114 of pad 100 permits, in essence, change from an inwardly directed position of angled (or curved) lateral side surface 40 to the generally vertical lateral side surface 52. It may be desirable to practice such an arrangement alone, or together with another exemplary member 16, during some uses of the subject invention.

Also, other shapes and sizes of the respectively paired opposite lateral side walls may be provided. In such case, the caregiver may select the desired lateral wall shape and size to be placed adjacent the patient, and removably secure the adjustable side rail or rails accordingly, per the present invention.

In addition, it may be observed from the exemplary configuration of present FIG. 7 that side rail means 14 does not need to extend the entire length of the resilient base member 100. While matched lengths may be the case in given embodiments (such as in FIG. 1), member 14 may have a shorter length along longitudinal axis 30, in some embodiments, than base member 100, and still provide adequate protection for the needs of a given patient. In the illustrated embodiment of FIG. 7 wherein base member 100 has an exemplary longitudinal length of about 26 inches, side rail member 14 is shown as having the same dimensions as represented for it in present FIG. 1. For example, member 14 may have a longitudinal length of about 19 inches, a height (the vertical height of lateral side wall 52) of about 3 inches, and a base width (the lateral width of lower support surface 34) of about 3 and ⅜ inches. Other dimensions may be practiced in other embodiments, for example resulting in a three inch height for lateral side wall 52 and a likewise 3 inch width for lower support surface 34. In such an embodiment, the angle or the radius of curvature of lateral side wall 40 is adjusted so as to properly intersect with the location of edge 48 in relation to its width from opposing lateral side wall 52.

FIG. 7 represents a still further alternative feature in accordance with the subject invention, wherein the first securement means or the first layer of material comprises an enclosure generally 116. Such enclosure comprises a fabric layer encasement removably received about the entire base member 100, the fabric of which may comprise a brushed knitted fabric suitable for securement thereto of hook elements of the hook and eye (i.e., "Velcro") complementary type securement elements. With such an arrangement, again continuously variable repositioning of components is provided in relation to upper support surface 102.

Hook and eye complementary type securement elements 118 and 120, respectively, may also be practiced in a "zipper" type arrangement adjacent one end edge of enclosure 116. Alternatively, snaps, or an actual zipper, or other means may be utilized to enclose same.

Such a fabric layer encasement 116 is preferred in the instance of a base member 100 having contour cut or other specific patient support surface features other than a generally flat surface as in the case of base member 12. By having a looser fitting arrangement, rather than an adhesively attached arrangement (as with layers 24, 26, and 28 of FIG. 1), the benefit of the individual patient support cells is preserved.

In addition, an optional protective casing, such as a plastic element, film, or the like, 122, may be provided internal to encasement 116, for incontinent or other protection. In some embodiments, such an incontinent protection may be omitted, which will permit the base member 12 or 100 to act with a sponge effect as to any bodily fluids, or other fluids which may be present in an incubator chamber, or otherwise present under patient care conditions.

Figure 8:
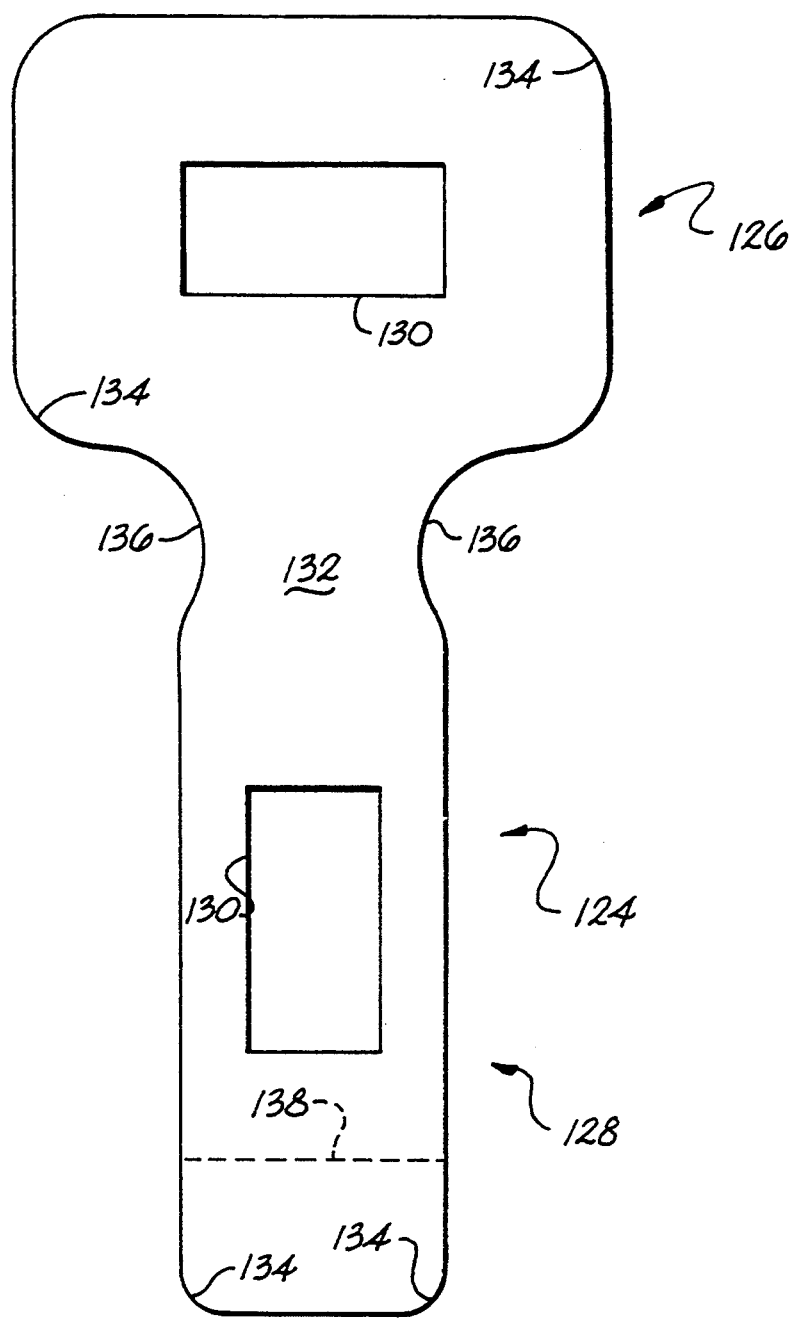
FIG. 8 shows a bottom plan view of a further pillow means embodiment in accordance with the subject invention, as a further alternative to the exemplary embodiment of present FIGS. 5 and 6, such as also for supporting the head and torso of a pediatric patient.

It will be understood by those of ordinary skill in the art that still further variations may be practiced in accordance with the subject invention. For example, present FIG. 8 illustrates a bottom plan view of a still further exemplary pillow generally 124 which may be practiced in accordance with the subject invention. Such specific embodiment 124 is intended as an alternative to the embodiment of present FIGS. 5 and 6, and again comprises essentially a T-shaped cross-section with a relatively broadened first section 126 thereof generally for supporting a patient's head and with a relatively elongated second section 128 thereof generally for supporting a patient's torso. Patches 130 of hook-type securement elements (not shown), may be provided on a generally planar lower support surface 132 for securing such pillow means 124 to a generally planar patient support surface, such as surface 22 of present FIG. 1 or surface 102 of present FIG. 7.

Preferably pillow 124 is comprised of resilient foam material, generally with the characteristics stated by way of various ranges above, or in some instances with other characteristics. Dimensionally, pillow means 124 will also fall within the ranges broadly stated with reference to present FIGS. 5 and 6.

As to the specific exemplary embodiment of present FIG. 8, an overall exemplary thickness thereof preferably may be about 1.75 inches, with an exemplary longitudinal length of about 15 inches. Generally head supporting section 126 may have an exemplary longitudinal length of about 5 inches and an exemplary lateral width of about 6.75 inches, while generally torso supporting region 128 may have a lateral width of about 3 inches.

As illustrated throughout FIG. 8, in comparison with present FIG. 5, the FIG. 8 embodiment of pillow means 124 has more rounded edges, such as edges 134 and at other contours thereof (such as at section intersections 136), by which improved comfort may be provided in the instance of specific care situations for specific pediatric patients. As noted above, still further alternative pillow arrangements may be practiced in accordance with the subject invention.

As to methodology of use, those of ordinary skill in the art will appreciate the multiple adjustment features provided by various embodiments in accordance with the subject invention, and how such may be selectively utilized in a given patient instance. For example, any one of the three pillow embodiments (pillow means 32 of present FIG. 4; pillow means 70 of present FIGS. 5 and 6; or pillow means 124 of present FIG. 8) may be selected and then appropriately positioned under the preselected patient body portion corresponding with the predetermined contoured shape of the selected patient pillow. Each of the pillow embodiments have a generally flat bottom support surface, preferably with one of hook and eye complementary type securement elements thereon, so as to seat properly on a patient support surface in accordance with the subject invention.

Also, variations may be practiced by a caregiver, by way of modifications to a given pillow. For example, a caregiver may trim the size of elongated second section 128 of pillow 124 by cutting, such as along exemplary dotted line 138, to fit the size of a given patient. Therefore, the placement of securement features 130 may be selected so as to accommodate subsequent caregiver modifications.

Still further, one or more side rail elements in accordance with the subject invention may be appropriately selected and positioned so that a desired lateral side wall thereof is desirably removably secured for protectively partially enclosing a pediatric patient on such upper support surface without impeding caregiver access to such patient.

Likewise, present methodology is intended to encompass all modifications and variations to use of the slits and removable segments situated in the upper side wall surfaces of the present adjustable side wall members, for facilitating operative interaction of a patient with technical support thereof (for example, patient treatment tubing and interconnecting lead lines). With the exception of instances whenever specific removable segments are removed from top wall surfaces of the adjustable side wall members, all other features of the subject invention may be subsequently assessed and readjusted to periodically accommodate changes in patient care conditions of course, even the removal of a given removable segment does not preclude otherwise remaining subsequent rearrangements of the adjustable patient treatment tube securement features disclosed in accordance with the subject invention.

It should be further understood by those of ordinary skill in the art that the foregoing presently preferred embodiments are exemplary only, and that the attendant description thereof is likewise by way of words of example rather than words of limitation, and their use does not preclude inclusion of such modifications, variations, and/or other additions to the present invention as would be readily apparent to one of ordinary skill in the art, the scope of the present invention being set forth in the appended claims.

What is claimed is:

1. An adjustable pediatric incubator nest, comprising:
   a resilient base member, having an upper support surface for receiving a pediatric patient thereon, and having first securement means provided on said upper support surface for removably securing further nest members thereto at selected positions thereon; and
   a pair of resilient foam adjustable side wall members, having respective lower support surfaces with respective second securement means thereon for selectively cooperating with said first securement means for removably securing said side wall members to said base member upper support surface, with said side wall members adjustably positioned in substantially opposing relationship to one another at a selected interval, so that said side wall members protectively partially enclose a pediatric patient on said upper support surface without impeding caregiver access to such patient.

2. An adjustable pediatric incubator nest as in claim 1, wherein:
   said base member comprises a generally rectangular foam member; and
   said first securement means comprises a layer received on said upper support surface and including a fabric with a preselected surface texture for selective securement of said side wall members thereto.

3. An adjustable pediatric incubator nest as in claim 2, wherein:
   said side wall members have respective upper side wall surfaces which are at a predetermined height above said base member upper support surface in a range generally from about 2 inches to about 5 inches;
   said rectangular base member has a predetermined thickness of generally at least about 1 inch, a predetermined width in a range generally from about 10 inches to about 15 inches, and a predetermined length in a range generally from about 15 inches to about 30 inches; and
   said foam comprising said base member and said side wall members has a predetermined density in a range generally from about 1 to about 1.6 pounds per cubic foot and a 25% ILD characteristic in a range generally from about 10 pounds to about 30 pounds, where 25% ILD characteristic means the number of pounds of pressure required as an indenting load on a 50 square inch circular plate to deflect a foam member under such plate 25% of the unloaded predetermined thickness of such foam member.

4. An adjustable pediatric incubator nest as in claim 3, wherein said first and second securement means comprise respective one of hook and eye complementary type securement elements.

5. An adjustable pediatric incubator nest as in claim 4, wherein:
   said upper side wall surfaces include tube receiving slits, integrally formed therein and extending a predetermined depth downwardly towards said respective lower supports surfaces, adapted to receive patient treatment tubes passed therethrough for providing a removable interference fit therewith, said slits being spaced at predetermined intervals along said upper side wall surfaces so as to further integrally form therein selectively removable side wall segments for the passage of relatively larger diameter patient treatment tubes therethrough; and
   further wherein said side wall members each have a respective lateral side wall which has a predetermined slope thereto so that such sloped lateral side walls may be situated relatively opposite to one another with a patient received therebetween on said base member upper support surface.

6. An adjustable pediatric incubator nest as in claim 5, further including at least one patient pillow comprising a predetermined shaped resilient foam member with third securement means thereon for selectively cooperating with said first securement means for removably securing said pillow to said base member upper support surface, with said pillow adapted to adjustably support a selected body region of a patient received on said upper support surface.

7. An adjustable pediatric incubator nest as in claim 6, wherein said predetermined shape of said pillow includes a contoured upper pillow surface with at least one relative lobe for supporting a patient's neck and at least one relative trough for supporting a patient's head.

8. An adjustable pediatric incubator nest as in claim 6, wherein said predetermined shape of said pillow includes a generally T-shaped cross-section with a relatively broadened first section thereof generally for supporting a patient's head and with a relatively elongated second section thereof generally for supporting a patient's torso.

9. An adjustable pediatric incubator nest as in claim 2, wherein said first securement means comprises an enclosure including a fabric layer encasement removably received about said base member, the fabric of which comprises a brushed knitted fabric suitable for securement thereto of hook elements of hook and eye complementary type securement elements.

10. An adjustable pediatric incubator nest as in claim 9, wherein:
   said base member upper support surface comprises a contour cut patient support surface with a plurality of individual patient support cells integrally formed in regular patterns of aligned rows therein and with air channels integrally formed between adjacent of said aligned rows of cells;
   said side wall members have respective upper side wall surfaces which are at a predetermined height above said base member upper support surface in a range generally from about 2 inches to about 5 inches;

said rectangular base member has a predetermined thickness of generally at least about 1 inch, a predetermined width in a range generally from about 10 inches to about 15 inches, and a predetermined length in a range generally from about 15 inches to about 30 inches;

said foam comprising said base member and said side wall members has a predetermined density in a range generally from about 1 to about 1.6 pounds per cubic foot and a 25% ILD characteristic in a range generally from about 10 pounds to about 30 pounds, where 25% ILD characteristic means the number of pounds of pressure required as an indenting load on a 50 square inch circular plate to deflect a foam member under such plate 25% of the unloaded predetermined thickness of such foam member; and wherein said first and second securement means comprise respective one of hook and eye complementary type securement elements.

11. An adjustable pediatric incubator nest as in claim 10, wherein:

said upper side wall surfaces include tube receiving slits, integrally formed therein and extending a predetermined depth downwardly towards said respective lower support surfaces, adapted to receive patient treatment tubes passed therethrough for providing a removable interference fit therewith, said slits being spaced at predetermined intervals along said upper side wall surfaces so as to further integrally form therein selectively removable side wall segments adapted to pass relatively larger diameter patient treatment tubes therethrough; and further wherein said side wall members each have a respective lateral side wall which has a predetermined slope thereto so that such sloped lateral side walls may be situated relatively opposite to one another adapted to receive a patient therebetween on said base member upper support surface.

said nest further including at least one patient pillow comprising a predetermined shaped resilient foam member with third securement means thereon for selectively cooperating with said first securement means for removably securing said pillow to said base member upper support surface, with said pillow adapted to adjustably support a selected body region of a patient received on said upper support surface.

12. An adjustable pediatric incubator nest as in claim 1, further including patient treatment tube securement means, integrally formed with said side wall members, adapted to removably and adjustably secure at least one patient treatment tube passed therethrough.

13. An adjustable pediatric incubator nest as in claim 12, wherein:

each of said side wall members have at least one angled lateral side wall, extending generally upwardly at an angle from said lower support surface, and terminating in a respective upper side wall surface further defined by each of said side wall members; and wherein said respective upper side wall surfaces each have a plurality of slits integrally formed therein and extending a predetermined depth downwardly from said upper side wall surfaces, said slits integrally forming a plurality of selectively removable side wall member segments between adjacent slits such that one or more of said segments may be selectively removed for the passage of relatively larger diameter patient treatment tubes therethrough, while said slits are otherwise adapted to receive relatively smaller diameter patient treatment tubes passed therebetween for providing an adjustable and removable interference fit therewith.

14. A multi-piece infant foam cradle, comprising:

a main support base comprised of resilient foam and having an infant support surface formed on an upper side thereof;

a first layer of material received on said support base upper side and providing a surface texture for selective securement of further cradle components thereto;

at least one adjustable side rail means comprising a generally elongated resilient foam member with securement means thereon for selectively positioned removable securement of said at least one adjustable side rail means to said first layer of material, such that said at least one adjustable side rail means adjustably protects an infant received on said infant support surface; and pillow means comprising a resilient foam member with securement means thereon for selectively positioned removable securement of said pillow means to said first layer of material, such that said pillow means is adapted to adjustably support a selected body region of an infant received on said infant support surface.

15. A multi-piece infant foam cradle as in claim 14, wherein said main support base upper side is generally flat and provides a relatively planar infant support surface.

16. A multi-piece infant foam cradle as in claim 14, wherein said main support base upper side has a plurality of individual foam cells defined therein with air channels formed between adjacent such cells, said cells providing a relatively planar infant support surface.

17. A multi-piece infant foam cradle as in claim 16, wherein said first layer of material comprises washable fabric removably encasing said main support base.

18. A multi-piece infant foam cradle as in claim 14, wherein:

said main support base is generally rectangular and has a predetermined thickness; and said first layer of material surface texture and said securement means comprise respective complementary ones of hook and eye complementary type securement elements.

19. A multi-piece infant foam cradle as in claim 18, wherein said pillow means foam member is contoured for supporting an infant's head and neck.

20. A multi-piece infant foam cradle as in claim 18, wherein said pillow means foam member is contoured for supporting an infant's head and torso.

21. A multi-piece infant foam cradle as in claim 18, wherein said adjustable side rail means elongated resilient foam member has an elongated generally flat bottom receiving said adjustable side rail means securement means thereon, and has an opposing pair of elongated lateral walls extending generally upwardly from said flat bottom and terminating in a top wall of said at least one adjustable side rail means, said top wall being formed at a generally predetermined height above said flat bottom.

22. A multi-piece infant foam cradle as in claim 21, wherein:

said opposing pair of elongated lateral walls includes a first wall which rises generally at an angle from said flat bottom and a second wall which rises generally vertically from said flat bottom, so that the position of said at least one adjustable side rail means may be selectively reversed on said main support base such that selectively one of said first and second lateral walls is directed towards an infant received on said infant support surface; and further wherein said top wall includes a plurality of slits formed therein adapted to receive tubes passed therethrough, with adjacent pairs of said slits defining a plurality of selectively removable segments for the passage of relatively larger diameter tubes therethrough.

23. A multi-piece infant foam cradle as in claim 22, wherein:

said cradle includes a second adjustable side rail means identical to said at least one adjustable side rail means, so that both of said adjustable side rail means may be respectively secured in mirrored positions on opposite sides of an infant received on said infant support surface; and further wherein said adjustable side rail means respective top walls are at said predetermined height above said respective flat bottoms thereof in a range generally from about 2 inches to about 5 inches;

said main support base has a predetermined thickness of generally at least about 1 inch, a predetermined width in a range generally from about 10 inches to about 15 inches, and a predetermined length in a range generally from about 15 inches to about 30 inches; and said foam comprising said main support base and said side rail means has a predetermined density in a range generally from about 1 to about 1.6 pounds per cubic foot and a 25% ILD characteristic in a range generally from about 10 pounds to about 30 pounds, where 25% ILD characteristic means the number of pounds of pressure required as an indenting load on a 50 square inch circular plate to deflect a foam member under such plate 25% of the unloaded predetermined thickness of such foam member.

24. A multi-piece multi-adjustable incubator nest for a neonatal ICU patient, said incubator nest comprising:

a generally rectangular base mattress comprising resilient foam of predetermined support characteristics and having an upper side patient support surface, said patient support surface having a predetermined arrangement of support elements formed therein and providing generally planar patient support;

a fabric layer received on said patient support surface and comprising fabric for one of hook and eye complementary type securement elements substantially covering said patient support surface;

a pair of generally elongated adjustable side rails comprising resilient foam and having respective curved side surfaces for positioning on opposite sides of a patient received on said patient support surface for protectively partially enclosing such patient, said side rails having respective generally flat bottom support surfaces with one of hook and eye complementary type securement elements thereon so that said side rails may each be selectively removably secured to said fabric layer positioned at desired respective locations on said patient support surface, and having respective top surfaces a predetermined distance above said bottom support surfaces thereof, said top surfaces including openings therein adapted to receive and secure treatment tubes and apparatus therethrough for an ICU patient supported in said incubator nest; and at least one patient pillow comprising resilient foam and having a predetermined contoured shape adapted to support a preselected corresponding body portion of a patient received on said patient support surface, said at least one pillow having a generally flat bottom support surface with one of hook and eye complementary type securement elements thereon so that said pillow may be selectively removably secured to said fabric layer positioned at a desired location on said patient support surface.

25. A multi-piece multi-adjustable incubator nest as in claim 24, wherein:

said side rails respective top surfaces are at said predetermined distance above said respective bottom support surfaces thereof in a range generally from about 2 inches to about 5 inches;

said rectangular base mattress has a predetermined thickness of generally at least about 1 inch, a predetermined width in a range generally from about 10 inches to about 15 inches, and a predetermined length in a range generally from about 15 inches to about 30 inches; and said foam comprising said base mattress and said side rails has a predetermined density in a range generally from about 1 to about 1.6 pounds per cubic foot and a 25% ILD characteristic in a range generally from about 10 pounds to about 30 pounds, where 25% ILD characteristic means the number of pounds of pressure required as an indenting load on a 50 square inch circular plate to deflect a foam member under such plate 25% of the unloaded predetermined thickness of such foam member.

26. A multi-piece multi-adjustable incubator nest as in claim 25, wherein said predetermined arrangement of support elements includes a plurality of contour cuts in said patient support surface, said contour cuts forming patient support surface segments with a predetermined amount of separation between adjacent said surface segments for air circulation.

27. A multi-piece multi-adjustable incubator nest as in claim 26, wherein said surface segments comprise individual support cells aligned in longitudinal and lateral rows in said patient support surface, said cells having relatively rounded edges at said patient support surface, and at least certain of said rows including generally circular air channels formed at the bases of adjacent individual support cells.

28. A multi-piece multi-adjustable incubator nest as in claim 25, wherein said fabric layer includes an encasement removably received about said base mattress, the fabric of which comprises a brushed knitted fabric suitable for securement thereto of hook elements of hook and eye complementary type securement elements.

29. A multi-piece multi-adjustable incubator nest as in claim 25, wherein said respective top surface openings comprise slits formed in said top surface and directed a predetermined depth generally towards said respective bottom support surfaces, said slits being selectively spaced so as to form removable segments between adjacent pairs of said slits.

30. A multi-piece multi-adjustable incubator nest as in claim 29, wherein adjacent of said slits are spaced at a predetermined distance in a range generally from about 0.5 inches to about 2 inches, and wherein said predetermined depth of said slits is in a range generally from about 0.5 inches to about 2 inches.

31. A multi-piece multi-adjustable incubator nest as in claim 29, wherein:
said predetermined arrangement of support elements includes a plurality of contour cuts in said patient support surface, said contour cuts forming patient support surface segments with a predetermined amount of separation between adjacent said surface segments for air circulation; and
wherein said fabric layer includes an encasement removably received about said base mattress, the fabric of which comprises a brushed knitted fabric suitable for securement thereto of hook elements of hook and eye complementary type securement elements.

32. A multi-piece multi-adjustable incubator nest as in claim 25, wherein said patient pillow has a contoured shape including two relative lobes and one relative trough adapted to support the head and neck of an ICU patient received thereon.

33. A multi-piece multi-adjustable incubator nest as in claim 32, wherein said patient pillow has a predetermined varying thickness falling in a range generally from about 0.5 inches to about 2 inches, a predetermined width in a range generally from about 3 inches to about 8 inches, and a predetermined length in a range generally from about 4 inches to about 10 inches.

34. A multi-piece multi-adjustable incubator nest as in claim 25, wherein said patient pillow has a generally T-shaped cross-section with a relatively broadened first section thereof generally adapted to support a patient's head and with a relatively elongated second section thereof generally adapted to support a patient's torso.

35. A multi-piece multi-adjustable incubator nest as in claim 34, wherein said patient pillow has a predetermined thickness in a range generally from about 0.5 inches to about 3 inches, a predetermined length in a range generally from about 6 inches to about 20 inches, a predetermined width in said relatively broadened first section thereof in a range generally from about 3 inches to about 8 inches, and a predetermined width in said relatively elongated second section thereof in a range generally from about 1 inch to about 5 inches.

36. A method of care for a neonatal ICU patient through use of a multi-piece multi-adjustable incubator nest, said method comprising:
providing an incubator nest including a generally rectangular base mattress of resilient foam and having an upper side patient support surface; a fabric layer received on said patient support surface and comprising fabric for one of hook and eye complementary type securement elements substantially covering said patient support surface; a pair of generally elongated adjustable side rails comprising resilient foam and having respective generally flat bottom support surfaces with one of hook and eye complementary type securement elements thereon; and at least one patient pillow comprising resilient foam and having a generally flat bottom support surface with one of hook and eye complementary type securement elements thereon;
selectively positioning said side rails on opposite sides of a patient received on said patient support surface with said side rails spaced from one another a selected distance so as to protectively partially enclose the patient without impeding caregiver access thereto;
removably securing said side rails in the selected positions thereof by pressing said respective side rail bottom support surfaces onto said fabric layer for engagement of the respective complementary type securement elements thereof;
selectively positioning said pillow so as to support a portion of the body of a patient received on said patient support surface;
removably securing said pillow in the selected position thereof by pressing said pillow bottom support surface onto said fabric layer for engagement of the respective complementary type securement elements thereof; and
periodically subsequently assessing and adjusting the selected positions of said side rails and said pillow so as to optimize patient care in an ICU incubator in which the patient is received.

37. A method as in claim 36, wherein:
said providing step further includes providing said pair of side rails with respective top surfaces having a plurality of spaced slits therein which form a corresponding plurality of removable foam segments across the top of said side rails; and
said method further includes the step of arranging relatively smaller diameter patient treatment tubes and apparatus leads in said nest removably seated in selected ones of said slits, and arranging relatively larger diameter patient treatment tubes and apparatus leads in said nest by selectively cutting out selected ones of said removable foam segments and removably seating such tubes or leads in the areas where segments have been removed.

38. A method as in claim 37, wherein said providing step further includes making a plurality of contour cuts in said patient support surface so as to form therein a corresponding plurality of individual support cells with predetermined spacing therebetween for air circulation, and includes providing said fabric layer as an encasing cover of brushed knitted material removably received on said base mattress.

39. A method as in claim 37, wherein:
said providing step further includes providing said pair of side rails respectively each with a lateral side wall which is situated at an angle between said respective bottom support and top surfaces of each side rail; and
said step of selectively positioning said side rails includes placing said side rails such that the respective angled lateral side walls thereof face inwardly towards a patient received in the ICU incubator.

40. A method as in claim 37, wherein:
said providing step further includes providing said pair of side rails each with a respective opposing pair of lateral side walls extending generally upwardly from each respective bottom support surface and terminating in each respective top surface, with each respective opposing pair including a first lateral side wall which rises generally at an angle from its respective bottom support surface and a second lateral side wall which rises generally vertically from its respective bottom support surface; and
said step of selectively positioning said side rails includes placing said side rails so that a selected one of said first and second lateral side walls of each side rail is facing inwardly towards a patient received in the ICU incubator.

41. A method as in claim 39, wherein:

said providing step further includes providing respective first and second patient pillows, each having a generally flat bottom support surface with one of hook and eye complementary type securement elements thereon, and each having a respective predetermined contoured shape for supporting a preselected corresponding body portion of a patient received on said patient support surface; and said step of selectively positioning said pillow includes selecting which of said first and second patient pillows to use, and positioning the selected patient pillow under the preselected patient body portion corresponding with the predetermined contoured shape of such selected patient pillow.

* * * * *